United States Patent
Li et al.

(10) Patent No.: US 9,180,078 B2
(45) Date of Patent: Nov. 10, 2015

(54) COSMETIC COMPOSITION CONTAINING LINGONBERRY EXTRACT AND ITS USES

(71) Applicants: Chunhua Li, Beijing (CN); Yanmei Li, Beijing (CN)

(72) Inventors: Chunhua Li, Beijing (CN); Yanmei Li, Beijing (CN)

(73) Assignee: BEIJING GINGKO GROUP BIOLOGICAL TECHNOLOGY CO., Beijing (CN)

( * ) Notice: Subject to any disclaimer, the term of this patent is extended or adjusted under 35 U.S.C. 154(b) by 37 days.

(21) Appl. No.: 13/935,455

(22) Filed: Jul. 3, 2013

(65) Prior Publication Data

US 2013/0296418 A1    Nov. 7, 2013

Related U.S. Application Data

(62) Division of application No. 12/667,205, filed on Jun. 8, 2010, now Pat. No. 8,501,246.

(51) Int. Cl.

| | |
|---|---|
| *A01N 65/00* | (2009.01) |
| *A61K 8/49* | (2006.01) |
| *A61K 8/34* | (2006.01) |
| *A61Q 19/00* | (2006.01) |
| *A61Q 19/08* | (2006.01) |
| *A23L 1/30* | (2006.01) |
| *A61K 36/00* | (2006.01) |
| *A61Q 19/02* | (2006.01) |
| *A61K 8/97* | (2006.01) |

(52) U.S. Cl.
CPC ............... *A61K 8/498* (2013.01); *A23L 1/3002* (2013.01); *A61K 8/347* (2013.01); *A61K 8/97* (2013.01); *A61K 36/00* (2013.01); *A61Q 19/00* (2013.01); *A61Q 19/02* (2013.01); *A61Q 19/08* (2013.01); *A61K 2800/92* (2013.01)

(58) Field of Classification Search
CPC ..................................................... A61K 36/00
USPC .......................................................... 424/725
See application file for complete search history.

(56) References Cited

U.S. PATENT DOCUMENTS

2006/0134299 A1 *   6/2006   Lahteenmaki ................ 426/590

OTHER PUBLICATIONS

Lingonberry, 1 page, 2014.*
Favorable effects, 2 pages, 2008.*
"Cellulose", 2014, 2 pages.*

* cited by examiner

*Primary Examiner* — Michael Meller

(57) ABSTRACT

The invention relates to a cosmetic composition containing lingonberry extract and its use on skin cosmetology thereof. The present invention has provided a lingonberry extract wherein containing polyphenols components including anthocyanidin, procyanidin, resveratrol, catechin and so on. The present invention also relates to the application of lingonberry extract on skin cosmetology, including without limitation whitening, diminishing visible pigmentation, anti-wrinkle, moisturizing, smoothing and improving skin sensitivity. The invention also has revealed drugs, cosmetic compositions and food prepared by using lingonberry extract. Comparing with the prior art cosmetic compositions, the said lingonberry extract of the present invention has higher effects and safe.

4 Claims, No Drawings

COSMETIC COMPOSITION CONTAINING LINGONBERRY EXTRACT AND ITS USES

CROSS-REFERENCE TO RELATED APPLICATIONS

This application is a divisional application, claiming the priority of co-pending U.S. patent application Ser. No. 12/667,205, filed Apr. 10, 2008, which claims priority to PCT Application Number PCT/CN2008/000740, entitled An Extract of *Vaccinium Vitis Ideaea* L. and Pharmaceutical Composition, Cosmetic Composition, Food and Use Thereof, filed on Apr. 10, 2008.

DESCRIPTION

1. Field of the Invention

The invention relates to a lingonberry extract and its uses in cosmetology. The present invention provides a lingonberry extract which contains anthocyanidin about 5~35 wt %, procyanidin about 20~80 wt %, resveratrol about 0.01~5.0 wt %. The present invention also relates to the application of the lingonberry extract in cosmetology, including but not limited to whitening, diminishing visible pigmentation, anti-wrinkle, moisturizing, smoothing and improving skin sensitivity. The present invention also relates to drugs, cosmetic compositions and foods containing the lingonberry extract. Comparing with the prior art cosmetic compositions, the lingonberry extract of the present invention has higher effects and safety.

2. Description of the Related Art

Lingonberry (*Vaccinium vitis-idaea* L.) also named Hongdou, Xiaopingguo, Yageda, Xiongguoye in China, which belongs to Ericaceae *Vaccinium*, is perennial hardwood or evergreen shrub or dwarf shrub. Lingonberry, originally growing in mountain areas of Northeast of China, Former Soviet Union, North Korea, North America and North Europe, which mixed-grows with blueberry, is a kind of evergreen dwarf shrub. The height of the tree is about 5~30 cm with evergreen herbaceous leaves. It has strong ability of cold and drought Resistance. The fruit of lingonberry with bright red color and sour-puckery flavor is good to pulmonary and has high value in use.

Japanese patent application JP3826698B2 disclosed a cosmetic composition which was made from extract of lingonberry leaves and fruits compounding with other excipients. The lingonberry extract disclosed in that patent was gained by the following steps: using lingonberry's leaves and fruits as raw material to extract with alcohol-water solution, condensing the extract solution, handling the extract solution with resin. But deficients of the extract made by the method of the patent are: (i) the extract's ingredients being complicated and uses limited for the mixed raw material composed of lingonberry's leaves and fruits; (ii) only for external use; (iii) wasting materials as the method cannot extract the effective ingredients sufficiently in lingonberry.

PCT application WO2006134583 disclosed a cosmetic composition having lingonberry extract. But the invention still used a extract of lingonberry's leaves and fruits (occupying about 50% individually), which still had the deficiencies of Japanese patent JP3826698B2 and also only was for external use.

As a result, there is a demand on safe lingonberry extract with good efficacy. And at the same time, lingonberry extract applications are needed to be exploited further. Thereby the effective ingredients of lingonberry extract are needed to be more identified, whose safety and efficacy should be proved and usage fields should be expanded.

SUMMARY OF THE INVENTION

The aim of the present invention is to provide lingonberry extract to overcome one of problems of the prior art mentioned above.

The lingonberry extract extracting method provided in the present invention can be the same as conventional method, including but not limiting to the art disclosed in Chinese patent application CN101077864A, which is incorporated here as reference.

A preferable method to produce lingonberry extract includes following steps:

(1) Extracting, using the fruit of lingonberry as raw material, with aqueous acid at normal temperature, or with aqueous alcohol at normal or lower temperature, and then filtrating to obtain lingonberry extract solution;

(2) Purifying the lingonberry extract solution obtained in step (1) by resin (3) Drying the said purified exact obtained in step (2) to get lingonberry exact part field in anthocyandin;

(4) Refining pomace obtained in step (1) after extracting with aqueous acid or aqueous alcohol and filtrating by silica gel column chromatography separation to get lingonberry compound rich in resveratrol;

(5) Mixing lingonberry exact part rich in anthocyandin and the said lingonberry exact part rich in resveratrol at appreciable proportion to obtain three kinds of lingonberry extract, which are lingonberry extract I, II and III respectively. Lingonberry extract I contains anthocyandin about 15%, procyanidin about 60% and resveratrol about 0.01%; lingonberry extract II contains anthocyandin about 5%, procyanidin about 10% and about resveratrol 20%; lingonberry extract contains anthocyandin about 10%, procyanidin about 35% and resveratrol about 10%.

The main compounds in the said lingonberry extracts are detected by the following methods:

(1) A HPLC method for detecting anthocyandin in lingonberry

Chromatographic column: ODS-AQ 250×4.6 mm, 5 μm
Mobile phase: phase A, water: formic acid=90:10;
  Phase B, water:acetonitrile:methanol:formic acid=45: 22.5:22.5:10
  Gradient Condition:

| | Time (min) | | | | | | | | | |
|---|---|---|---|---|---|---|---|---|---|---|
| | 0.01 | 5 | 20 | 25 | 35 | 45 | 50 | 55 | 60 | 65 | 70 |
| B % | 18 | 18 | 20 | 25 | 25 | 35 | 18 | 40 | 60 | 60 | 18 |

Detection wave length: 535 nm (2) A HPLC method for detecting resveratrol in lingonberry Chromatographic column: ODS-AQ 250×4.6 mm, 5 μm
Mobile phase: Phase A.: methanol;
  Phase B: 0.2% formic acid
  Gradient Conditions:

| time (min) | Mobile Phase A (%) | Mobile Phase B (%) |
|---|---|---|
| 0-25 | 18 | 82 |
| 25-30 | 18-30 | 82-70 |
| 30-50 | 30 | 70 |

Detection wave length: 303 nm.

(3) A tartaric acid or Folin-C method for detecting resveratrol in lingonberry.

The lingonberry extract of the present invention is preferably selected from the lingonberry fruits extract.

The present invention also relates to a cosmetic use of at least one of the said lingonberry extract in present invention.

The said lingonberry extract of the present invention can also be exploited as a series of cosmetic products. Skin is a kind of connective tissue containing collagen protein and elastin which are both important to the whole structure of skin. Moderate cross linkage of collagen is good to maintain integrity of skin. Whereas oxidation from free radical in vivo can make the collagen over cross link, and as a result wrinkle and vesicle appear on the serface of the skin. The lingonberry extract of the present invention can improve the moderate cross linkage of collagen protein and clear free radical efficiently to keep skin from aging, remaining white and bright. In addition, elastin can make skin resilient. If there is not enough elastin, the skin will be relaxation to appear old. Elastin can be degradated by free radicals and elastase. The lingonberry extract of the present invention can clear the free radicals, block emergence and activity of elastase to improve the condition of skin. Researching on skin hydroxyproline content and SOD activity of skin photoaging mice by ultraviolet radiation, it is revealed that the hydroxyproline content and SOD activity of the mice taking the said lingonberry extract of the present invention are all higher obviously than the model group, which illustrates that the lingonberry extract can protect the skin collagen protein through its excellent anti-oxidation to appear anti-wrinkle and anti-aging function on cosmetology.

Otherwise, other use of lingonberry extract of the present invention on cosmetology are also disclosed, including but not limitating to whitening, diminishing visible pigmentation, anti-wrinkle, moisturizing, smoothing and improving skin sensitivity.

The lingonberry extract of the present invention used as an ideal melanogenesis suppressant has characteristics as follows:

(1) The lingonberry extract can cure hyperpigmentation effectively;
(2) The lingonberry extract has no cytotoxicity on melanocytes, epidermal cells and hypodermal cells;
(3) The lingonberry extract has no sensitization, carcinogenicity and teratogenicity;
(4) The lingonberry extract has good stability.

The lingonberry extract of present invention can be made without limitation to capsules, tablets and oral liquid etc.....

The lingonberry extract of the present invention can also be made into many kinds of foods, such as beverage, wine, cake, candy, gum and so on.

In addition, aside from the components especially mentioned above, the preparation of the present invention should include conventional excipients or carriers of the prior art.

In an embodiment, the cosmetic products have the lingonberry extract of the present invention about 0.0001 wt %~100 wt %, preferably about 0.0 wt %~30 wt %, more preferably about 0.1 wt %~15 wt %.

In an embodiment of the present invention, the lingonberry extract can be taken orally. The dosage is 1 mg/kg~5 mg/kg per day and usually 60 mg/day~300 mg/day for adults.

The present invention also provides a cosmetic composition taken orally containing the lingonberry extract as active component. The composition can be made into both solid preparations including tablet, capsule, soft capsule, honeyed pill, powder, granule, and liquid preparations including oral liquid, cream, syrups ea.

The cosmetic composition of the present invention can also be incorporated into candy, gum, soup powder, dairy products, beverages and so on. The specific examples of the above mentioned foods include gum, candy, chocolate, jelly, cookies, puffed food, broth powder, milk, yoghurt, ice cream, lactic acid beverage, spirits, vitamin beverage, mineral beverage, coffee beverage, function beverage and so on. When the lingonberry extract is incorporated into the above foods, the proper amount is about 0.0001 wt %~100 wt %, preferably is about 0.01 wt %~30 wt %, more preferably is about 0.1 wt~15 wt %.

The present invention also provided a cosmetic or skin care composition used as whitening containing the lingonberry extract as active component. The cosmetic or skin care composition of the present invention may also have common adjuvants adding in cosmetic or skin care products, such as hydrophilic or oleophylic gelling agent, hydrophilic or oleophylic activator, antiseptics, anti-oxidant, solvent, perfuming agent, sunscreen agent, pigment, fragrant absorbent and colorant. The person skilled in the relevant field can select the dosage of adjuvants according to need.

When the said cosmetic or skin care composition is made into cream, lipid-phase-ratio usually is about 5~80 wt % of the total weight, preferably is about 5~50 wt %, such as, but not limit to, about 10 wt %, about 20 wt %, about 30 wt %, about 40 wt % and so on. The oil, emulsifier and co-emulsifier used in the cream composition can be the common material of the relevant field. The ration of emulsifier and co-emulsifier in the cream is usually about 0.3~30 wt % of the total, preferably is about 0.5~20 wt %.

The lingonberry extract of the present invention can be combinedly used with the following kinds of oil: mineral oil, plant resource oil (such as soya oil), animal resource oil (such as agnolin), synthesis oil (such as perhydro-squalene). Besides, fatty alcohol, fatty acid and wax can also be used as fatty material.

The lingonberry extract of the present invention can be combinedly used with the following kinds of emulsifier and co-emulsifier: fatty acid ester (such as macrogol) and fatty acid ester of glyceric such as stearin.

According to an embodiment of the present invention, the lingonberry extract can also be used at least one kind of activator, including but not limiting to ellagic acid and its derivatives, hydroquinol, arbutin, resorcin and its derivatives, vitamin C and its derivatives, pantothenic acid sulfonate and its derivatives, cojic acid, intacellin, molecules that can interfera α-melanotropin (α-MSH) or its receptors or actone (ACTH), polyhydroxy compound (such as glycerine, ethylene alcohol or propylene glycol), vitamin, ceratin dissolving agent or decorticate agent (such as ortho-oxybenzoic acid and its derivate), α-alcoholic acid (such as lactic acid or malic acid), antiscorbic acid and its derivatives, retinoic acid, retinal, retinol and its derivate, anti-inflammatory agent, emollient and its mixture, chemical or physical sunscreen agent (such as micronization zinc oxide, titanium oxide, butyl-methoxyl-dibenzoyl-methane and octyl methoxycinnamate), deoxyribose nucleic acid and nucleic acid.

In a word, the present invention provides:
1. A lingonberry extract containing anthocyanidin about 5~35 wt %.
2. A lingonberry extract containing procyanidine about 20~80 wt %.
3. A lingonberry extract containing polyphenols about 5~100%, wherein the polyphenols are selected from the group consisting of anthocyanidin, procyanidin, flavone, anthoxanthin, catechinic acid, epicatechin and its polymeride.
4. A lingonberry extract containing resveratrol about 0.01~50 wt %.
5. The lingonberry extract according to item 4 mentioned above further comprising polyphenols about 5~100%, wherein the said polyphenols can be selected from the group consisting of anthocyandin, procyanidin, flavone, catechin, epicatechin and its polymeride.
6. A lingonberry extract containing anthocyanidin mentioned about 5~35 wt %, procyanidin about 20~80 wt %, resveratrol about 0.01~50 wt %.
7. The application of the lingonberry extract according to 1~6 mentioned above on drugs preparation, wherein the said drugs can be used in prevention or treatment of monophenolase activity abnormality syndrome.
8. A drug composition containing the lingonberry extract according to items 1~6 mentioned above, wherein the said drug composition can be used to inhibit the activity of monophenolase.
9. The drug composition according to item 8 mentioned above, wherein the percentage of the said lingonberry extract is about 0.0001 wt %~100 wt % of the total weight.
10. The application of the lingonberry extract according to items 1~6 mentioned above on preparation of cosmetic or skin care composition.
11. The said application according to item 10 mentioned above, wherein the said cosmetic or skin care composition can be applicated on melanogenesis inhibition, clearance on skin pigmentation, colored spot and acne.
12. The said application according to item 10 mentioned above, wherein the said cosmetic or skin care composition can be applicated on aging skin renovation, skin moisture content elevation, skin flexibility enhancement, anti-wrinkle and anti-aging.
13. The said application according to item 10 mentioned above, wherein the cosmetic or skin care composition can be applicated on skin smoothing and skin sensitivity regulation.
14. A cosmetic or skin care composition, wherein containing the said lingonberry extract according to items 1~6 mentioned above.
15. The cosmetic or skin care composition according to item 14 mentioned above, wherein also has other elements selected one or several from the group consisting of other kinds of fruit extract, collagen protein, hyaluronic acid, and other carrying agent and vehiculum that can be used in cosmetology, wherein the said other kinds of fruit extract can be selected from the group consisting bilberry extract, grape extract, pomegranate extract, *rosa roxburghii* extract, apple extract and kiwi fruit extract,
16. A kind of food having cosmetic function containing the lingonberry extract according to 1~6 mentioned above.
17. The food having cosmetic function according to item 16 mentioned above, further containing other components selected one or several from the group consisting of other kinds of fruit extract, collagen protein, hyaluronic acid, and other carrying agent and vehiculum that can be used in food, wherein the said other kinds of fruit extract can be selected from the group consisting of bilberry extract, grape extract, pomegranate extract, *rosa roxburghii* extract, apple extract and kiwi fruit extract.
18. The food having cosmetic function according to item 16 or 17 mentioned above, including without limitation candy, cake, soup powder, milk product and beverages.
19. A skin care method for applying the cosmetic or skin care composition according to item 14 or 15 mentioned above on the skin area needed treatment, or taking the food having cosmetic function orally according to item 17 or 18 mentioned above.

The following embodiments will explain the present invention further but should not be explained as the limit on the present invention.

DETAILED DESCRIPTION OF THE EMBODIMENTS OF THE INVENTION

Example 1

Preparation of Lingonberry Extract I 1000 g lingonberry fruit was immersed in 3-fold amount of water solution and added 0.1% cellulose water solution, then mixed. The mixture was incubated in 40° C. thermostatic waterbath for 2 hours, and then filtered to obtain an extract solution. The extract solution was filtered through an ultrafiltration membrane filter (molecular weight 2000) to obtain an concentrated solution. The concentrated solution after membrane filter was purified by HP20 macroporous resin, eluted with 60% ethanol, concentrated further and spray dried to obtain anthocyanidin part of lingonberry.

The fruit residue after the mentioned above steps was heated and extracted with 75% ethanol to obtain yellow cream. Then the cream was dealt with silica gel column chromatography to collect the resveratrol part of lingonberry.

The anthocyanidin part and resveratrol part were combined to gain lingonberry extract I, which comprised anthocyanidin about 15%, procyanidin about 60% and resveratrol about 0.01%.

Example 2

Preparation of Lingonberry Extract II 1000 g lingonberry fruit was extracted by 2% hydrochloric acid ethanol water solution at 40° C. to obtain an extract solution. The extract solution was treated by XAD16 macroporous resin columns directly and then washed by 90% ethanol to obtain the eluant. The eluant was dealt with vacuum concentration to remove the ethanol and spray drying to obtain anthocyanidin part of lingonberry.

The fruit residue after the mentioned above steps was heated and extracted with ethanol to obtain yellow cream. Then the cream was dealt with silica gel column chromatography to collect the composition riching in resveratrol which was then recrysted with about 95% ethanol to obtain the resveratrol part of lingonberry.

The anthocyanidin part and resveratrol part were combined to gain lingonberry extract II, which comprised anthocyanidin about 5%, procyanidin about 10% and resveratrol about 20%.

Example 3

Preparation of Lingonberry Extract III 1000 g lingonberry fruit was extracted by 60% ethanol water solution at 40° C. to obtain an extract solution. After retrieving the ethanol, the extract solution was treated by CHPA20 ion exchange resin and then washed with ethanol about 90% to obtain the eluant. The eluant was dealt with vacuum concentration to remove the ethanol and spray drying to obtain anthocyanidin part of lingonberry.

The fruit residue after the mentioned above steps was heated and further extracted with 95% ethanol to obtain yellow cream. Then the cream was dealt with silica gel column chromatography to collect the composition riching in resveratrol.

The mentioned above anthocyanidin part and resveratrol part were combined to gain lingonberry extract III, which comprise anthocyanidin about 10%, procyanidin about 35% and resveratrol about 10%.

Example 4

Comparison between Influences of Lingonberry Extract and Arbutin on Cell

B16 melanocytes (from SIBCB) were cultivated with RPMI-1640 culture fluid containing about 10% newborn calf serum and penicillium_streptomycin under the condition of about 37° C., about 5% $CO_2$. Digest the melanocytes with about 0.125% trypsin (Difco, US) when the cell fusion reached more than about 80%.

The activity of melanocytes multiplication was determined by measurement of trititaed thymidine incorporation (MTT). The B16 melanocytes at densities of about $1\times10^5$ were inoculated in 24-well cell cultured plate. The culture fluid was changed next day and the tested substances in different concentration were added individually: the lingonberry extract III prepared in example 3 (comprised anthocyanidin about 10%, OPC about 35% and resveratrol about 10%), arbutin bought from the market, and blank as control group.

After 20 hours cultivation and adding about 0.15 ml MTT, the cells were cultivated continuously for about 4 hours. Centrifuged at 3000 rpm for about 10 min and deserted the supermatant, cultivated cells in every well were added DMSO (about 1%) about 1 ml and shooked for dissolving thoroughly. Then about 150 μl cultivated cells aspiration were added into 96-well cell cultured plate. The OD value of the aspiration was measured with MQX200 micro-plate spectrophotometer (Bio-Tek, US), at 570 nm excitation wave length and 630 nm reference wave length.

Calculated the inhibition ratio of tested agents on melanocytes using the following formula:

melanocytes multiplication inhibition ratio=(1−OD of tested group/OD of control group)*100%

The results were shown in Table 1:

TABLE 1 comparison of influence on cell survival ratio between arbutin and lingonberry extract (%, $\bar{x} \pm SD$, n = 6)

| Concentration (mg/L) | arbutin | lingonberry extract |
|---|---|---|
| blank | 100.00 ± 1.03 | 100.00 ± 0.82 |
| 20 | 110.72 ± 0.41 | 139.47 ± 1.63 |
| 40 | 94.30 ± 0.45 | 122.46 ± 0.66 |
| 60 | 91.74 ± 0.39 | 118.20 ± 0.48 |
| 80 | 79.66 ± 1.08 | 112.59 ± 0.86 |

It can be seen from table I that at the same concentration the cell survival ratios of lingonberry extract tested groups are all higher than the arbutin groups which indicates that lingonberry extract has more lower toxicity on B16 cells than arbutin and as a result is more safer than the latter.

Example 5

Comparative Study on Cell Multiplication Influences of Lingonberry Extract, Grape seed Extract and Pine Bark Extract The experimental method was the same as example 4. The lingonberry extract III was prepared by the method in example 3, pine bark extract and grape seed extract were both bought from market, blank was used as control group. The results was showed as the following table 2.

TABLE 2 comparison of influence on cell survival ratio of three kinds of extract (%, $\bar{x} \pm SD$, n = 6)

| Dosage (mg/L) | Pine bark extract | Grape seed extract | Lingonberry extract |
|---|---|---|---|
| blank | 100.00 ± 0.71 | 100.00 ± 0.71 | 100.00 ± 0.71 |
| 1 | 93.57 ± 2.33 | 99.85 ± 0.38 | 102.57 ± 1.87 |
| 5 | 95.91 ± 0.90 | 102.51 ± 0.12 | 111.34 ± 1.11 |
| 25 | 105.85 ± 0.20 | 105.78 ± 0.46 | 153.99 ± 1.15* |

*P < 0.05;
**P < 0.01 vs control group

It can be seen from table 2 that the influences of pine bark extract, grape seed extract and lingonberry extract at different level of concentration on B16 cell survival ratio are almost the same, which is augmentation according to the extracts' concentration and presents evident dose-response relationship. It can be concluded that these three kinds of extract are all safe to cells in vitro.

Example 6

Comparative Study on Inhibition Rate of B16 Melanocytes' Tyrosinase Activity of Lingonberry Extract, Grape Seed Extract, Pine Bark Extract and Arbutin B16 melanocytes (from SIBCB) were cultivated with RPMI-1640 culture fluid containing 10% newborn calf serum and penicillium_streptomycin under the condition of about 37° C., 5% $CO_2$. The melanocytes were digested with about 0.125% trypsin (Difco, US) to be passaged or tested when the cell fusion reached more than 80%.

Tyrosinase activity is determined by the speed of dopa being oxidized into dopaquinone. L-dopa was used as catalysis substrate. Optical density (OD) of dopaquinone was determined at 475 nm by improved Marlinez-Esparza method. (Ando H, Itoh A, Mishima Y et al., Correlation between the number of melanosomes, tyrosinase mRNA levels, and tyrosinase activity cultured murine melanoma cells in response to various melanogenesis regulatory agents. J Cell Physiol, 1995, 163: 608-614.). The higher of the OD, the stronger of the tyrosinase.

The lingonberry extract III was prepared by the method in example 3, other materials were all bought from market.

After 3 days of effection of tested substance, the supernatant was deserted and the remainer was washed for 3 times with pH 7.0 PBS after centrifuging at 1000 rpm for 5 mm every time. The cells were dissolved by 1% Troton X-100 400 μl adding in every well of the cultured plate, 100 μl solution in every well was taken and then added into 96-well cultured plate. After pre-temperature at 37° C., 100 μl 1.7% L-dopa (sigma, US) was added into every well. The OD A value then was determined every 10 min within 1 hour at 475 nm and 37° C., using blank as zero adjustment.

Calculated every tested agents' inhibition rate of B16 melanocytes' tyrosinase activity using the following formula:

inhibition rate of melanocytes' tyrosinase activity=(1−OD of tested group/OD of control group)*100%

The results was showed as the following table 3.

TABLE 3 comparison of influence on inhibition rate of melanocytes' tyrosinase activity of different kinds of extract ($\bar{x} \pm SD$, n = 6)

| Concentration (mg/L) | Lingonberry extract | Pine bark extract | Grape seed extract | Arbutin |
|---|---|---|---|---|
| 1 | 5.98 ± 1.36 | 1.98 ± 1.36 | −1.02 ± 0.12 | 7.19 ± 0.00 |
| 5 | 10.99 ± 0.61 | 5.74 ± 1.75 | −1.53 ± 0.61 | 10.43 ± 2.97 |
| 10 | 18.62 ± 1.41 | 14.15 ± 1.99 | 11.22 ± 3.35 | 20.50 ± 1.63 |
| 20 | 46.21 ± 0.56 | 31.98 ± 6.00 | 25.51 ± 4.61 | 46.40 ± 2.53 |
| 30 | 61.08 ± 0.38 | 40.57 ± 3.01 | 40.81 ± 4.10 | 53.29 ± 2.27 |

It can be seen from table 3 that the influences of four kinds of substances on inhibition rate of melanocytes' tyrosinase activity are all more and more stronger with the increasing of their concentration. Whereas the rising amplitude of lingonberry extract test group is more obvious. When the concentration is about 30 mg/L, the inhibition rate of lingonberry extract on melanocytes' tyrosinase activity is much higher than other tested groups.

Example 7

Comparative Study on B16 Melanogenesis Influences of Lingonberry Extract, Grape Seed Extract, Pine Bark Extract and Arbutin's B16 melanocytes (from SIBCB) were cultivated with RPMI-1640 culture fluid containing about 10% newborn calf serum and penicillium_streptomycin under the condition of 37° C., 5% $CO_2$. The melanocytes were digested with about 0.125% trypsin (Difco, US) to be passaged or tested when the cell fusion reached more than about 80%.

After the cells dissolved in strong base solution, melanin was dissolved and then the OD was tested. Melanin content was determined by Hosoi improved method. (Victoria M, Virador, Nobuhiko Kobayashi et al, A standardized protocol for assessing regulators of pigmentation. Analytical Biochemistry, 1999, 270:207~219.)

B16 melanocytes (1×10$^5$) were cultivated in 6-well cultured plate. After 24 hours incubation the solution was changed and different kinds of tested substances in different concentration were added respectively. The lingonberry extract III was prepared by the method in example 3, other substances were all bought from market.

After 72 hours, reactants were washed by PBS for 2 times, dried by air-drying dissolved into 400 μl 1N NaOH (containing 1% DMSO), heated at 80° C. for 1 hour and then cooled. The OD was tested by enzyme-linked immunosorbent assay instrument at 475 nm.

Calculated every tested agents' inhibition rate of melanin content using the following formula:

inhibition rate of melanin content=[1−(OD of tested group/well cell density of tested group)/(OD of control group/well cell density of control group)] *100%

The results was showed as the following table 4.

TABLE 4 comparison of influence on inhibition rate of melanin content of different kinds of extract ($\bar{x} \pm SD$, n = 4)

| concentration (mg/L) | Lingonberry extract | Pine bark extract | Grape seed extract | Arbutin |
|---|---|---|---|---|
| 1 | −1.09 ± 0.22 | −4.27 ± 0.78 | −1.02 ± 5.12 | 7.27 ± 2.29 |
| 5 | 1.99 ± 0.00 | −3.66 ± 1.94 | 0.82 ± 1.03 | 7.59 ± 0.35 |

TABLE 4-continued comparison of influence on inhibition rate of melanin content of different kinds of extract ($\bar{x} \pm SD$, n = 4)

| concentration (mg/L) | Lingonberry extract | Pine bark extract | Grape seed extract | Arbutin |
|---|---|---|---|---|
| 10 | 7.14 ± 0.09 | −1.02 ± 4.37 | 5.73 ± 2.78 | 6.23 ± 0.86 |
| 20 | 20.76 ± 0.53 | 0.2 ± 2.77 | 16.36 ± 1.23 | 10.80 ± 0.33 |
| 30 | 30.04 ± 0.30 | 3.05 ± 0.41 | 39.26 ± 1.81 | 12.07 ± 1.30 |

It can be seen from table 4 that pine bark extract has no apparent inhibiting effect on melanogenesis, whereas the inhibition rate of the other three kinds of substances were increasing gradually with the increasing of their concentration. When the concentration reached to 30 mg/L, lingonberry extract and grape seed extract's inhibition rates of melanogenesis reached to 30.04% and 39.26% respectively, which were all much higher than arbutin group.

Example 8

Comparative Study on Inhibition Rate of B16 Melanocytes' Tyrosinase Activity Influencing by Different Kinds of Lingonberry Extract Experiment method was the same as example 6. The lingonberry extract I, II and III used as tested substance were prepared by the method in example 1, 2 and 3 respectively.

The result was showed in table 5.

TABLE 5 comparison of influence on inhibition rates of melanocytes' tyrosinase activity of different kinds of extract ($\bar{x} \pm SD$, n = 6)

| concentration (mg/L) | Lingonberry extract □ | Lingonberry extract □ | Lingonberry extract □ |
|---|---|---|---|
| 1 | 3.11 ± 0.13 | 2.06 ± 0.12 | 5.98 ± 1.36 |
| 5 | 4.33 ± 0.61 | 5.38 ± 1.65 | 10.99 ± 0.61 |
| 10 | 11.54 ± 1.30 | 10.36 ± 1.66 | 18.62 ± 1.41 |
| 20 | 35.64 ± 4.33 | 30.75 ± 5.20 | 46.21 ± 0.56 |
| 30 | 52.17 ± 4.99 | 49.78 ± 3.96 | 61.08 ± 0.38 |

It can be seen from table 5 that inhibition rates of melanocytes' tyrosinase activity of different kinds of extract were augmenting with the increasing of the extracts concentration and presented evident dose-response relationship. When the concentration <10 mg/L, the influence was not obvious. When concentration was higher than about 20 mg/L, three kinds of extract's inhibition rates of melanocytes' tyrosinase activity all increased obviously, whereas the influence of lingonberry extract III was more stronger than others.

Example 9

Comparative Study Among on B16 Melanogenesis Influences of Different Kinds of Lingonberry Extract Experiment method was the same as example 7. The lingonberry extract I, II and III used as tested substance were prepared by the method in example 1, 2 and 3 respectively.

The result was showed in table 6.

TABLE 6 comparison on inhibition rate of melanogenesis of different kinds of extract ($\bar{x} \pm SD$, n = 4)

| Concentration (mg/L) | Lingonberry extract☐ | Lingonberry extract☐ | Lingonberry extract☐ |
|---|---|---|---|
| 1 | −1.00 ± 0.52 | −0.27 ± 0.80 | −1.09 ± 0.22 |
| 5 | 0.98 ± 1.02 | 2.00 ± 1.05 | 1.99 ± 0.00 |
| 10 | 5.67 ± 2.05 | 6.03 ± 2.37 | 7.14 ± 0.09 |
| 20 | 16.36 ± 2.53 | 17.2 ± 2.57 | 20.76 ± 0.53 |
| 30 | 25.69 ± 2.33 | 23.05 ± 2.41 | 30.04 ± 0.30 |

It can be seen from table 6 that inhibition rates of melanogenesis of different kinds of extract are augmentation with the rising of the extract's concentration, whereas the effect of lingonberry extract is more obvious.

Example 10

Lingonberry Extract's Influence on Skin Photoaging Mice's SOD Activity and Hydroxyproline (HYP) Content 50 Kunming mice, weight 15~20 g, were divided into 5 groups randomly, that were control group, model group, tested group (high dosage, middle dosage, low dosage). Besides control group, mice of other groups, shaved the hair on back, were all exposed under UVA light everyday to result in photoaging model. The animals of high dosage, middle dosage and low dosage tested groups were given lingonberry extract (containing anthocyanidin about 12.9%, procyanidin about 60.3% and resveratrol about 10.1%) 160 mg/kg, 80 mg/kg and 40 mg/kg respectively, whereas animals of control group were given distilled water of the same volume. After animals sacrificed 8 weeks later, full-thickness skin of the hair-shaved site on the back was taken at once and sop activity & HYP content of the local site were determined by biochemistry method. The result was showed in the following table 7.

TABLE 7

Influence of Lingonberry Extract on Skin SOD and HYP of Photoaging Model Mice

|  | SOD (NU/mg prot) | HYP (nmol/mg prot) |
|---|---|---|
| Control group | 44.73 ± 6.98* | 2.96 ± 0.71* |
| Model group | 11.42 ± 2.55 | 1.00 ± 0.24 |
| High dosage | 25.36 ± 3.45* | 2.88 ± 0.70* |
| Middle dosage | 20.26 ± 4.19* | 2.52 ± 0.67* |
| Low dosage | 22.18 ± 3.98* | 1.90 ± 0.60 |

*$P < 0.05$, vs model group

It can be seen that lingonberry extract can restrain the photoaging procedure of skin and elevate the skin SOD activity and HYP content to make skin vigorous and flexible again. As a result, it can be added into health products with cosmetic effects and cosmetics.

Example 11

Lingonberry Extract Capsule's Effect on Skin

Lingonberry extract I, II and III were made into capsules, which had the extract 150 mg respectively. 39 female volunteers aging 22~55 were divided into three groups, given lingonberry extract I, II and III respectively 1 capsule/d. Wrinkle grade, colored spot, skin sensitivity, smoothing degree, skin color under RGB light and water content under UV light (system unit, more little value more light skin wrinkle grade) were tested before taking capsule and after taking capsule for 8 weeks by certain facial spectrometer. The skin surface wrinkled value, colored spot area, sensitivity, smoothing degree, skin color, water content before and after capsule taking are compared to analyze the lingonberry extract capsules's effect on anti-wrinkle, spot removing, skin sensitivity improving, skin smoothing improving, whitening and moisturizing. The result of human clinical experiment was showed in the following table 8.

TABLE 8

Clinical experimental result of lingonberry extract I, II and III effect on cosmetology

| | extract I | | | | extract II | |
|---|---|---|---|---|---|---|
| Item | before $\bar{X} \pm SD$ | After $\bar{X} \pm SD$ | P | Effective rate (%) | before $\bar{X} \pm SD$ | after $\bar{X} \pm SD$ |
| Wrinkle grade | 8.52 ± 8.12 | 7.75 ± 7.56 | 0.069 | 87.50 | 8.52 ± 8.12 | 9.48 ± 8.06 |
| Colored spot area | 14.48 ± 9.33 | 13.24 ± 8.73 | 0.045* | 87.50 | 19.73 ± 8.44 | 18.55 ± 7.68 |
| Skin sensitivity | 4.93 ± 4.60 | 3.21 ± 3.26 | 0.026* | 87.50 | 5.68 ± 5.04 | 5.78 ± 6.74 |
| Skin smoothing | 12.94 ± 7.77 | 10.02 ± 6.64 | 0.024* | 87.50 | 14.83 ± 7.60 | 14.12 ± 6.88 |
| Skin color | 19.52 ± 6.28 | 11.66 ± 5.18 | 0.0002** | 100 | 21.23 ± 8.67 | 23.45 ± 17.12 |
| Skin water content (UV) | 24.36 ± 3.60 | 21.66 ± 4.20 | 0.412 | 62.50 | 23.08 ± 7.48 | 23.22 ± 4.77 |

TABLE 8-continued

Clinical experimental result of lingonberry extract I, II and III effect on cosmetology

| | extract II | | Extract III | | | |
|---|---|---|---|---|---|---|
| Item | P | Effective rate (%) | before $\bar{X} \pm SD$ | after $\bar{X} \pm SD$ | P | Effective rate (%) |
| Wrinkle grade | 0.102 | 62.31 | 8.33 ± 6.89 | 7.36 ± 7.12 | 0.019* | 94.12 |
| Colored spot area | 0.286 | 62.31 | 19.73 ± 8.44 | 15.47 ± 9.00 | 0.028* | 94.12 |
| Skin sensitivity | 0.738 | 62.31 | 5.68 ± 5.04 | 4.32 ± 5.93 | 0.015* | 94.12 |
| Skin smoothing | 0.908 | 54.62 | 14.83 ± 7.60 | 11.36 ± 6.38 | 0.044* | 82.35 |
| Skin color | 0.076 | 70.00 | 21.23 ± 8.67 | 12.16 ± 5.09 | 0.000007** | 100 |
| Skin water content (UV) | 0.631 | 54.62 | 23.08 ± 7.48 | 24.61 ± 4.15 | 0.006** | 100 |

*$P < 0.05$;
**$P < 0.01$ vs before

It can be seen from the result that extract I, II and III all have the effect of relieving facial wrinkle and diminishing visible pigmentation, improving skin sensitivity and smoothness, whitening and moisturizing effects. All these indexes have distinguished statistical significance compared with the value before capsule taking ($P<0.05$) and the total effective rates are all higher than 87%. Lingonberry extract III can obviously relieve the facial wrinkle grade and colored spot, improve skin sensitivity and smoothness. All these indexes have distinguished statistical significance compared with the value before capsule taking ($P<0.05$) and the total effective rates are all higher than 82%. Lingonberry extract III especially has significant effect on whitening and moisturizing. Those two indexes have distinguished statistical significance compared with the value before capsule taking ($P<0.01$) and the total effective rates reaches 100%.

Experiment 12

Candies Having Cosmetic Function Made from Lingonberry Extract

The candies were made obeying the traditional composition proportion showed by the following table 9.

TABLE 9

| Lingonberry extract III made in example 1 | 15 wt % |
|---|---|
| Sugar | 50 wt % |
| Starch syrup | 30 wt % |
| Antiscorbic acid | 3 wt % |
| Menthol | 1.0 wt % |
| Colorant, food flavor | 1.0 wt % |
| Total | 100 wt % |

Example 13

A Health Food Having Cosmetic Function Containing Lingonberry Extract

The health food having cosmetic function containing lingonberry extract was made obeying the traditional composition proportion showed by the following table 10.

TABLE 10

| Lingonberry extract III made in example 1 | 10~15 wt % |
|---|---|
| Grape seed extract | 2.5~5 wt % |
| Bilberry extract | 2.5~5 wt % |
| Collagen protein powder(containing amino acids 85%) | 5~10 wt % |
| Soybean isoflavone | 5~10 wt % |
| Antiscorbic acid | 2~5 wt % |
| Sodium Hyaluronate | 1~3 wt % |
| Manna sugar | 15~35 wt % |
| Other excipients | 20~30 wt % |
| Total | 100 wt % |

The characteristic of the present invention is, for using lingonberry fruit especially as raw material, the extract can be taken orally directly. As a result, the bioavailability of the extract can be raised. Although explanatory embodiments have been shown and described, it would be appreciated by those skilled in the art that changes, alternatives, and modifications can be made in the embodiments without departing from spirit and principles of the present invention. Such changes, alternatives, and modifications all fall into the scope of the claims and their equivalents. As a result, it is obvious that the embodiments described herein are explanatory, illustrative, and used to generally understand the present invention, which shall not be construed to limit the present invention.

We claim:
1. A cosmetic tablet or capsule consisting essentially of a hydrochloric acid extract of lingonberry fruit and a component selected from the group consisting of *rosa roxburghii* extract, bilberry extract, grape extract, pomegranate extract, apple extract, kiwi extract, collagen, and hyaluronic acid.
2. The cosmetic tablet or capsule of claim 1, wherein said hydrochloric acid extract of lingonberry fruit contains at least one of anthocyanidin, procyanidin and resveratrol.
3. The cosmetic tablet or capsule of claim 1, wherein said hydrochloric acid extract of lingonberry fruit contains anthocyanidin in the range of 5-35 wt. % and procyanidin in the range of 20-80 wt. %.

4. The cosmetic tablet or capsule of claim 1, wherein said hydrochloric acid extract of lingonberry fruit contains anthocyanidin in the range of 5-35 wt. %, procyanidin in the range of 20-80 wt. % and resveratrol in the range of 0.01-50 wt. %.

* * * * *

UNITED STATES PATENT AND TRADEMARK OFFICE
CERTIFICATE OF CORRECTION

| | | |
|---|---|---|
| PATENT NO. | : 9,180,078 B2 | Page 1 of 1 |
| APPLICATION NO. | : 13/935455 | |
| DATED | : November 10, 2015 | |
| INVENTOR(S) | : Chunhua Li and Yanmei Li | |

It is certified that error appears in the above-identified patent and that said Letters Patent is hereby corrected as shown below:

On the title page item (73), "LTD." was omitted from the name of the Assignee, and the correct name of the Assignee should be "BEIJING GINGKO GROUP BIOLOGICAL TECHNOLOGY CO., LTD."

Signed and Sealed this
Twenty-ninth Day of March, 2016

Michelle K. Lee
*Director of the United States Patent and Trademark Office*